(12) United States Patent
Bokrantz et al.

(10) Patent No.: US 10,441,812 B2
(45) Date of Patent: Oct. 15, 2019

(54) SYSTEM AND METHOD FOR DETERMINING A RADIATION TREATMENT PLAN AND A RADIATION THERAPY MACHINE

(71) Applicant: RaySearch Laboratories AB, Stockholm (SE)

(72) Inventors: Rasmus Bokrantz, Stockholm (SE); Björn Hårdemark, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 565 days.

(21) Appl. No.: 15/367,872

(22) Filed: Dec. 2, 2016

(65) Prior Publication Data

US 2017/0157423 A1 Jun. 8, 2017

(30) Foreign Application Priority Data

Dec. 3, 2015 (EP) .................................... 15197756

(51) Int. Cl.
*A61N 5/10* (2006.01)

(52) U.S. Cl.
CPC ........... *A61N 5/1038* (2013.01); *A61N 5/103* (2013.01); *A61N 5/1036* (2013.01); *A61N 5/1045* (2013.01); *A61N 5/1047* (2013.01); *A61N 5/1071* (2013.01)

(58) Field of Classification Search
CPC ...................................................... A61N 5/10
See application file for complete search history.

(56) References Cited

U.S. PATENT DOCUMENTS

| | | | | |
|---|---|---|---|---|
| 7,142,635 B2* | 11/2006 | Kamath | ............... | A61N 5/1042 378/65 |
| 7,266,175 B1 | 9/2007 | Romesberg | | |
| 8,952,346 B2* | 2/2015 | Dempsey | ............. | A61N 5/1045 250/267 |
| 2005/0254623 A1* | 11/2005 | Kamath | ............... | A61N 5/1042 378/65 |

(Continued)

*Primary Examiner* — Thomas R Artman
(74) *Attorney, Agent, or Firm* — Drinker Biddle & Reath LLP (57) ABSTRACT

An output radiation treatment plan for at least one target in a treatment volume is determined. Each target is associated with a prescribed radiation dose. An updated treatment plan causes the prescribed radiation dose to be delivered to the target when implemented by a radiation therapy machine. The updated treatment plan requires an updated delivery time to complete and is calculated by:
 [i] receiving a numerical value designating an upper bound on modulation efficiency of the updated treatment plan,
 [ii] receiving a current treatment plan,
 [iii] calculating a current delivery time for the current treatment plan,
 [iv] calculating an un-modulated delivery time for the current treatment plan, and
 [v] calculating the updated treatment plan by executing an optimization process while satisfying the upper bound on the modulation efficiency.
Steps [ii] to [v] are traversed a predetermined number of times. Thereafter, the output radiation treatment plan is generated.

24 Claims, 3 Drawing Sheets

(56) References Cited

U.S. PATENT DOCUMENTS

2014/0275696 A1\* 9/2014 Dempsey ............. A61N 5/1045
                                                600/1
2015/0165233 A1\* 6/2015 Dempsey ............. A61N 5/1045
                                                250/492.1

\* cited by examiner

SYSTEM AND METHOD FOR DETERMINING A RADIATION TREATMENT PLAN AND A RADIATION THERAPY MACHINE

RELATED APPLICATION DATA

This application claims priority under 35 U.S.C. § 119 and/or § 365 to European Patent Application No. 15197756.8 filed Dec. 3, 2015, the entire contents of which is incorporated herein by reference.

THE BACKGROUND OF THE INVENTION AND PRIOR ART

The present invention relates generally to radiation therapy and strategies for programming a radiation therapy machine, in particular a photon radiation therapy machine also referred to as a linear accelerator. More particularly the invention relates to a system for determining a radiation treatment plan, a corresponding method and a radiation therapy machine. The invention also relates to a computer program product, a computer readable medium and a radiation therapy method.

Radiation therapy may be employed to treat tumorous tissue. In radiation therapy, a high-energy beam of radiation is aimed towards a patient. More precisely, a radiation source produces a beam of radiation that is collimated and directed into a target volume in the patient. The level and placement of the dose must be accurately controlled to, on the one hand, ensure that the tumor receives sufficient radiation; and, on the other hand, that damage to the surrounding healthy tissue is minimized. Before performing the radiation therapy, a radiation treatment plan is determined in a radiation planning session. This allows an accurate and precise dosage of radiation to be delivered to the patient.

However, it is far from trivial to establish an optimal radiation treatment plan. The radiation fields may need to be highly complex, in the sense that the apertures formed by the beam collimator are small and irregular, in order to render the radiation dose to conform closely to a tumor volume. Complex treatment plans generally have long treatment delivery times. This is undesirable under circumstances where clinical resources are limited, and because a prolonged delivery time means a greater patient exposure to harmful leakage and scatter radiation. Furthermore, a treatment plan of low complexity is advantageous compared with a more complex treatment plan because it is less sensitive to geometric errors, such as patient misalignment and organ motion, and easier to quality assure.

U.S. Pat. No. 7,266,175 describes a solution for controlling the correlation between the factors of treatment plan efficiency and dosimetric fitness to optimize the radiation therapy, or radiotherapy plan, including providing user control of the segment count, number of monitor units (MUs), and selection of an optimization algorithm.

Problems Associated with the Prior Art

Although the above solution may be useful to determine some aspects of treatment plan efficiency and dosimetric fitness, there is yet no solution that provides an unambiguous, or universally agreed upon, measure of the complexity of a radiation treatment plan.

SUMMARY OF THE INVENTION

The object of the present invention is therefore to solve the above problem, and offer a solution for determining a radiation treatment plan for a treatment volume, where the plan fulfills a well-defined complexity criterion.

According to one aspect of the invention, the object is achieved by the system of the preamble of claim 1, wherein the data processor is configured to: [i] receive a numerical value designating an upper bound on modulation efficiency of the updated treatment plan; [ii] receive a current treatment plan; [iii] calculate a current delivery time for the current treatment plan; [iv] calculate an un-modulated delivery time for the current treatment plan; and [v] calculate the updated treatment plan by executing an optimization process while satisfying the upper bound on the modulation efficiency.

The data processor is further configured to generate the output radiation treatment plan based on the updated treatment plan, for example after having traversed steps [ii] to [v] a predetermined number of times.

This system is advantageous because it provides a radiation treatment plan whose complexity is lower than or equal to an explicit and well-defined measure.

One advantage of the proposed bound on the modulation efficiency compared to a direct bound on the delivery time per treatment fraction, as such, is that the delivery time needed to produce an acceptable treatment plan depends on several parameters that are unrelated to plan complexity.

In particular, for a given total radiation dose, the fraction delivery time is inversely proportional to the number of treatment fractions. The fraction delivery time is also, for a given total dose, inversely proportional to machine dose rate. The fraction delivery time is directly proportional to the dose prescription, because a scaling of the fraction delivery time leads to a corresponding scaling of the fraction dose. The photon beam energy, which influences the relationship between absorbed radiation dose and number of MUs, is another parameter that affects the fraction delivery time but is unrelated to plan complexity.

According to one preferred embodiment of this aspect of the invention, the un-modulated delivery time is calculated based on an un-modulated delivery time per field of the current treatment plan. The un-modulated delivery time of a single field F, in turn, is a time required to deliver an un-modulated field $F_{UM}$ with an exposed fluence region equal to an exposed fluence region for the field F. Here, a fluence inside the exposed fluence region of the un-modulated field $F_{UM}$ has a constant value being scaled such that an average fluence is equal to an average fluence inside the exposed fluence region for the field F of the current treatment plan. The exposed fluence region is a sub-region of a beam plane to be exposed by an opening between a set of collimator leaves in a multi-leaf collimator of the radiation therapy machine during delivery of the field. This definition of the un-modulated delivery time provides a solid reference basis for the proposed complexity measure.

The proposed normalization of the delivery time of the current treatment plan against the delivery time of the un-modulated delivery time renders the modulation efficiency measure independent of the above-mentioned plan parameters. This property results in that the bound on modulation efficiency is comparatively easy to implement as a class solution across different patients, fraction schedules, and machine configurations.

Preferably, the upper bound on the modulation efficiency, in turn, represents a quotient between the updated delivery time and the un-modulated delivery time. The upper bound on the modulation efficiency is satisfied if the modulation efficiency is less than or equal to the numerical value. Hence, it is very straightforward for an operator to specify a desired degree of complexity for the radiation treatment plan.

Namely, he/she simply enters a number, say 3.4, into the system meaning that the output radiation treatment plan should have a delivery time whose duration is maximum 3.4 times the un-modulated delivery time.

According to another preferred embodiment of this aspect of the invention, the data processor is configured to traverse steps [ii] to [vi] repeatedly a particular number of times. Here, in an initial traversal, the current treatment plan represents an initial treatment plan for the treatment volume (i.e. a default plan). In each traversal subsequent to the initial traversal, the current treatment plan is the updated treatment plan obtained in a preceding traversal. Consequently, the current treatment plan improves gradually. At the same time, the upper bound on the modulation efficiency is satisfied throughout the process.

Preferably, the initial treatment plan represents one of the following: delivering uniform fluence profiles scaled so that an average radiation dose in the at least one target equals a highest prescription level of the respective prescribed radiation doses; delivering no radiation to the treatment volume; or delivering radiation to the treatment volume according to a previously generated output radiation treatment plan for the treatment volume, for example in agreement with a most recent prior therapy. Such default plans are advantageous because any of them will result in that the updated treatment plan converges into a useful plan in relatively few iterations.

According to a further preferred embodiment of this aspect of the invention, the data processor is configured to generate the output radiation treatment plan by completing at least one of the optimization phases: a fluence-map optimization phase, a leaf-sequencing optimization phase and a direct-machine-parameter optimization phase. In the fluence-map optimization phase, fluence per bixel are variables in the optimization process, each bixel being a surface element of a rectilinear fluence grid that discretizes the exposed fluence, defined such that the rows of the grid are aligned with the collimator leaves in the multi-leaf collimator. In the leaf-sequencing optimization phase, leaf event times are variables in the optimization process, each of said leaf event times defining a respective point in time when each leaf arrives at and leaves a bixel edge. In the direct-machine-parameter optimization phase, leaf positions, dose rate and delivery time per control point are variables in the optimization process. Moreover, the data processor is configured to apply steps [i] to [v] during execution of at least one of said at least one optimization phases. Thereby, the proposed strategy can be applied in or more phases of the entire process of establishing a radiation treatment plan for a patient, i.e. in the earliest phase, the final phase, as well as any phase in between.

According to another preferred embodiment of this aspect of the invention, the data processor is configured to calculate field delivery times depending on the phase to which the proposed strategy is applied. Specifically, in the fluence-map optimization phase, the data processor is configured to calculate a set of field delivery times. Here, in the set, each delivery time per field is a maximum delivery time per row of bixels in the fluence grid of the field. The delivery time of a row of bixels, in turn, is calculated as a sum of the delivery time for each bixel in the row. The delivery time per bixel is calculated as a sum of a leaf traversal time of the bixel and a positive difference between the irradiation time of the bixel and an irradiation time of a preceding bixel with respect to the direction of travel for the collimator leaves. The irradiation time for a bixel is defined as a fluence in the bixel divided by a dose rate of the radiation therapy machine. The leaf traversal time for a bixel is defined as a width of the bixel along the direction of leaf travel divided by a maximum leaf speed of the radiation therapy machine. In the leaf-sequencing optimization phase, the data processor is configured to determine a field delivery time calculated as a duration from a first leaf event until a last leaf event; and in the direct-machine-parameter optimization phase, the data processor is instead configured to calculate field delivery times as a sum of control point delivery times for a set of control points that belong to the field, the set of control points being the variables in the optimization process. Consequently, the upper bound on the modulation efficiency can be applied to any one of the main radiation treatment plan optimization phases in a straightforward manner.

According to still another preferred embodiment of this aspect of the invention, the data processor is configured to mitigate the upper bound on the modulation efficiency of the updated treatment plan by introducing a penalty term in the objective function that is to be minimized by the optimization. The penalty term measures a deviation from satisfying the upper bound on the modulation efficiency of the updated treatment plan. Hence, the upper bound on the modulation efficiency does not necessarily constitute a sharp limit. Instead, the bound may be exceeded somewhat given that the output radiation treatment plan is otherwise appropriate for one or more other reasons.

According to another preferred embodiment of this aspect of the invention, the data processor is configured to execute the optimization process under a first and/or second process. In the first process, the upper bound on the modulation efficiency is implemented with respect to a delivery time calculated as a sum of the delivery times for all fields and an un-modulated delivery time calculated as the sum of the un-modulated delivery times for all fields. In the second process, the upper bound on the modulation efficiency is implemented with respect to delivery time calculated as a sum of the delivery times for a subset of the fields and an un-modulated delivery time calculated as the sum of the un-modulated delivery times for the same subset of the fields. Thereby, the optimization with respect to the upper bound on the modulation efficiency may be effected on complete therapies as well as parts thereof.

According to yet another preferred embodiment of this aspect of the invention, the upper bound on the modulation efficiency includes a constraint on a set of optimization variables in addition to a number of constraints that are associated with causing the prescribed radiation dose to be delivered to the at least one target while aiming at not delivering more than a threshold amount of radiation to at least one organ-at-risk. Thus, the optimization with respect to the upper bound on the modulation efficiency can be combined with other important optimization aspects of radiation therapy.

According to another aspect of the invention, the object is achieved by the method of the preamble of claim 11, wherein the method further involves: [i] receiving a numerical value designating an upper bound on modulation efficiency of the updated treatment plan; [ii] receiving a current treatment plan; [iii] calculating a current delivery time for the current treatment plan; [iv] calculating an un-modulated delivery time for the current treatment plan; and [v] calculating the updated treatment plan by executing an optimization process while satisfying the upper bound on the modulation efficiency. Finally, the method also involves generating the output radiation treatment plan based on the updated treatment plan. The advantages of this method, as well as the preferred embodiments thereof, are apparent from the discussion above with reference to the proposed system.

According to a further aspect of the invention, the object is achieved by a computer program product according to the preamble of claim 22, which is loadable into the memory of a computer, and includes software for performing the steps of the above proposed method when executed on a computer.

According to another aspect of the invention, the object is achieved by a computer readable medium according to the preamble of claim 22, having a program recorded thereon, where the program is to make a computer perform the method proposed above when the program is loaded into the computer.

According to yet another aspect of the invention, the object is achieved by a radiation therapy machine according to the preamble of claim 21 configured to receive a radiation treatment plan generated by the above-proposed method, and carry out therapy in accordance with the received radiation treatment plan.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings, wherein.

DESCRIPTION OF PREFERRED
EMBODIMENTS OF THE INVENTION

Figure 1:
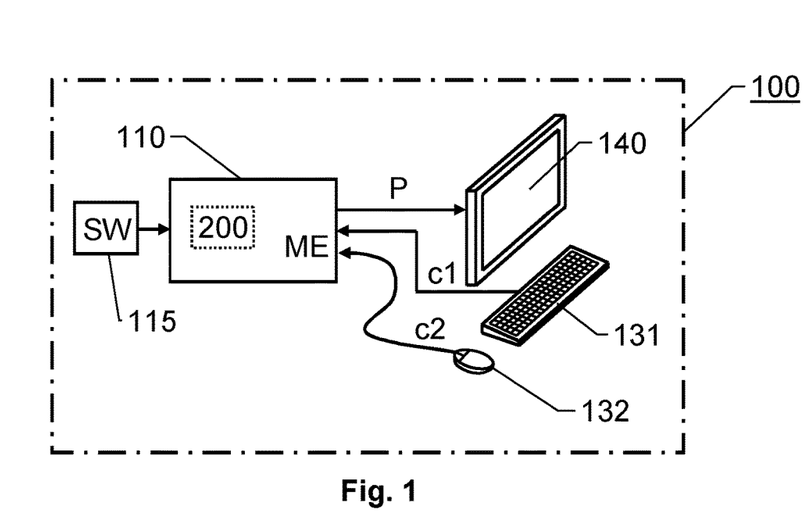
FIG. 1 shows a block diagram over a system according to one embodiment of the invention.
Figure 2:
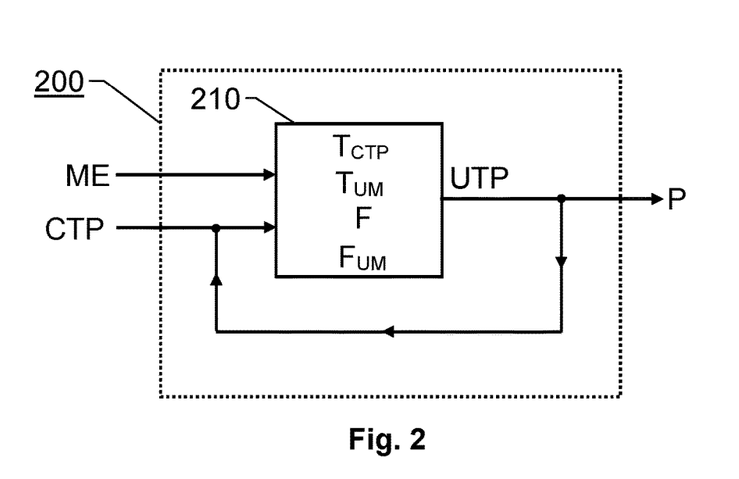
FIG. 2 illustrates an algorithm to be effected by a data processor of the proposed system.

Initially, we refer to FIGS. 1 and 2, where FIG. 1 shows a block diagram over a system 100 for generating an output radiation treatment plan P according to one embodiment of the invention, and FIG. 2 illustrates a proposed algorithm.

The output radiation treatment plan P is intended for a treatment volume associated with at least one target. Each of the at least one target, in turn, is associated with a respective radiation dose, for example prescribed by a physician as the amount of radiation deemed necessary to eradicate all tumor cells inside a particular target volume within a patient's body.

Usually, the output radiation treatment plan P is also intended to spare at least one organ-at-risk (i.e. healthy tissue), where the amount of radiation should be kept below certain levels not to cause unnecessary damages. This will be discussed further below, for instance with reference to FIG. 3.

The system 100 includes a data processor 110. Preferably, the system 100 also includes at least one first user interface 131 and 132 configured to receive operator commands c1 and c2 that specify a numerical value ME designating an upper bound on modulation efficiency of the output radiation treatment plan P. Consequently, the first user interface may contain input means, which in FIG. 1, are exemplified by a keyboard 131 (for entering text, numbers and commands) and a mouse 132 (for selecting and confirming selections). However, of course, according to embodiments of the invention, any other form of input means are equally well conceivable, e.g. a touchpad, a touch screen, a voice controlled interface and/or a gaze controlled interface. Further preferably, the system 100 includes at least one second user interface 140 (e.g. a graphical display) configured to present feedback data to the user, such as a description of the output radiation treatment plan P generated.

The data processor 110 is configured to calculate an updated treatment plan UTP, which when implemented by a radiation therapy machine is configured to cause the respective prescribed radiation dose to be delivered to the at least one target. It is presumed that the updated treatment plan UTP requires an updated delivery time $T_{UTP}$ to complete.

To calculate the updated treatment plan UTP, the data processor 110 is configured to [i] receive the numerical value ME, which, at this stage, designates an upper bound on modulation efficiency of the updated treatment plan UTP. However, since the data processor 110 is configured to generate the output radiation treatment plan P based on a final version of the updated treatment plan UTP, the numerical value ME also applies on the output radiation treatment plan P.

The data processor 110 is further configured to: [ii] receive a current treatment plan CTP; [iii] calculate a current delivery time $T_{CTP}$ for the current treatment plan CTP; [iv] calculate an un-modulated delivery time $T_{UM}$ for the current treatment plan CTP; and [v] calculate the updated treatment plan UTP by executing an optimization process while satisfying the upper bound on the modulation efficiency given by the numerical value ME.

Figure 3:
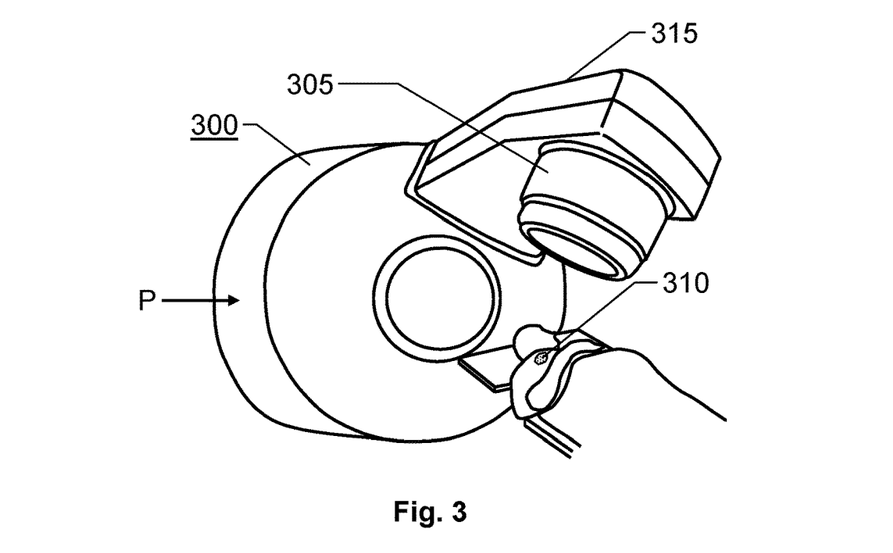
FIG. 3 shows a schematic radiation therapy machine according to one embodiment of the invention.

FIG. 3 schematically illustrates an example of a radiation therapy machine 300, which is configured to receive the output radiation treatment plan P determined by the system 100. The radiation therapy machine 300 is configured to carry out therapy in respect of the treatment volume 310 in a patient's body by controlling at least one radiation source 305 of the machine 300 in accordance with the output radiation treatment plan P.

As mentioned above, the output radiation treatment plan P is optimized to cause the prescribed radiation dose to be delivered to the at least one target while aiming at not delivering more than a threshold amount of radiation to at least one organ-at-risk. Preferably, the upper bound on the modulation efficiency also contains a constraint on a set of optimization variables in addition thereto. Thus, the optimization with respect to the upper bound on the modulation efficiency can be conveniently combined with other important optimization aspects of radiation therapy.

Figure 4:
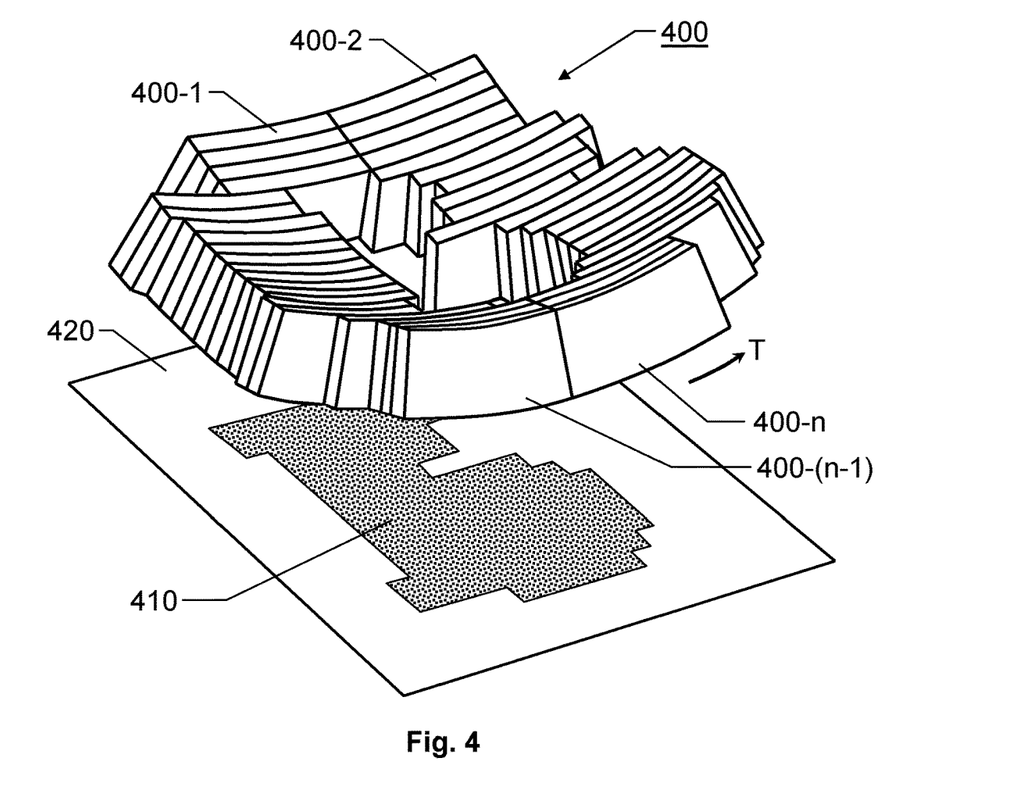
FIG. 4 shows an example of radiation beam, which is shaped by a multi-leaf collimator.

FIG. 4 shows an example of a multi-leaf collimator (MLC) 400, which may be used in the radiation therapy machine 300 as a blocking device to control the radiation from the at least one radiation source 305 therein, for instance a linear accelerator.

The MLC 400 has a set of collimator leaves 400-1, 400-2, . . . , 400-(n−1), 400-n, which are arranged as opposing pairs. Typically, each leaf has a width from 5 mm to 10 mm. The MLC 400 is arranged in the path of a radiation field F, and by adjusting the positions for the collimator leaves 400-1, 400-2, . . . , 400-(n−1), 400-n, a shape of an exposed fluence region 410 for the field F on a beam plane 420 can be altered, either continuously or in discrete steps.

The fluence transmitted through an opening in the MLC 400 is uniform at a given instance in time. However, a modulated fluence profile in the beam plane 420 can be generated by superposition in time of multiple fluences with different shapes of the opening in the MLC 400.

In dynamic multi-leaf collimation (DMLC) therapy, to which the invention is applicable, the collimator leaves 400-1, 400-2, . . . , 400-($n$–1), 400-$n$ are moved during irradiation.

In segmental multi-leaf collimation (or so-called step-and-shoot) treatment, to which the invention also is applicable, the collimator leaves 400-1, 400-2, . . . , 400-($n$–1), 400-$n$ are stationary during irradiation. Here, the radiation beam is switched off as the collimator leaves 400-1, 400-2, . . . , 400-($n$–1), 400-$n$ are repositioned.

Two important applications of DMLC treatment, in turn, are intensity-modulated radiation therapy (IMRT) and volumetric-modulated arc therapy (VMAT) treatments respectively.

An IMRT treatment is composed of a set of static beams that are delivered consecutively. The irradiation is here switched off as a gantry 315 holding the at least one radiation source 305 is rotated into position for a next beam.

The two-dimensional plane 420, which is perpendicular to a central axis of a particular beam passing through the opening in the MLC 400 is referred to as a beam plane. The beam planes, in turn, are discretized into rectangular surface elements called bixels. The rows in a bixel grid are assumed to be aligned with the collimator leaves 400-1, 400-2, . . . , 400-($n$–1), 400-$n$ of the MLC 400.

Treatment delivery for VMAT is performed with the gantry 315 continuously rotating during irradiation. Consequently, the therapeutic fluence is here instead delivered over an arc of up to 360 degrees. In VMAT, a radiation treatment plan can be composed of several, possibly overlapping, arcs.

Both IMRT and VMAT treatments are normally delivered over a set of identical treatment fractions, e.g., 30 daily fractions over the course of six weeks.

Today's standard for the IMRT-form of DMLC delivery is to construct MLC shapes by a sliding window, wherein the collimator leaves 400-1, 400-2, . . . , 400-($n$–1), 400-$n$ are moved unidirectionally across the beam plane along a given direction of travel T. This means that the opening between the opposing leaf pairs that transmits irradiation traverses the target volume 310 over the course of the field delivery. Typically, only a subset of the leaf pairs traverse the beam plane, for example the collimator leaves 400-1, 400-2, . . . , 400-($n$–1), 400-$n$, which intersect the beam's-eye-view projection of the target volume 310. The set of leaf pairs, which move within a field are referred to as the active leaf pairs. The active set of leaf pair indices is not necessarily consecutive, and any passive leaf pars are kept stationary and closed.

For a left-to-right sweep, an exposed fluence region is defined as a sub-region in the beam plane defined by the edges of the active leaf pairs, the start positions of the active left leaves, and the stop position of the active right leaves. Equivalently: an active left leaf is aligned with the left-side boundary of the exposed fluence region when the irradiation is switched on and an active right leaf is aligned with the right-side boundary of the exposed fluence region when the irradiation is switched off. It is common, but not necessary, that the active leaf pairs are positioned at the minimum dynamic leaf gap at the start and end time points of the beam delivery. Note that the exposed fluence region is composed of several disjoint geometric regions in the beam plane if the set of active leaf pairs is non-consecutive.

Sliding window can be applied also to VMAT treatments. Here, the leaf sweeps are performed over sub-intervals of an arc, with the direction of leaf movement alternated between consecutive gantry angle intervals.

"Field" is a collective term both for a static IMRT beam and a sub-interval of an arc. A distribution of fluence in the beam plane integrated over time is called the field's fluence profile. Note that a VMAT-field is unrelated to the gantry directions used for dose calculation. Fluence profiles can for example be defined by integration over 20 degree gantry angle intervals, while dose may be calculated over a gantry spacing of 2 degrees.

In the light of the above, the complexity of a radiation treatment plan can be expressed in terms of treatment delivery time, which, in turn, is defined as the sum of the beam-on times for each beam or arc during a single treatment fraction.

Therefore, if a relatively short treatment delivery time is desired, this implicitly leads to comparatively large and comparatively regular openings in the MLC 400. Namely, a large integral fluence per opening is necessary in order to cover the target volume with the prescription dose within a limited treatment delivery time.

For simplicity, at this stage, we consider radiation therapy machines with constant radiation output (or machine dose rate). The machine dose rate is measured in number of MUs per time unit. However, as will be touched upon below, the invention is also applicable to radiation treatment plans for machine with a variable dose rate.

Returning now to the above-mentioned step [iv], the un-modulated delivery time $T_{UM}$ is preferably calculated based on an un-modulated delivery time per field F of the current treatment plan CTP. The un-modulated delivery time per field F of the current treatment plan CTP, in turn, is the time required to deliver an un-modulated field $F_{UM}$ with an exposed fluence region equal to an exposed fluence region 410 for the field F of the current treatment plan CTP. A fluence inside the exposed fluence region 410 of the un-modulated field $F_{UM}$ has a constant value that is scaled such that an average fluence is equal to an average fluence inside the exposed fluence region 410 for the field F of the current treatment plan CTP.

The exposed fluence region 410 is a sub-region of the beam plane 420 to be exposed by the opening between the set of collimator leaves 400-1, 400-2, . . . , 400-($n$–1), 400-$n$ in the MLC 400 of the radiation therapy machine 300 during delivery of the field F.

According to one embodiment of the invention, the upper bound on the modulation efficiency (specified by the numerical value ME) represents a quotient between the updated delivery time $T_{UTP}$ and the un-modulated delivery time $T_{UM}$. The upper bound on the modulation efficiency is satisfied if the modulation efficiency is less than or equal to the numerical value ME.

According to one embodiment of the invention, the data processor 110 is configured to traverse steps [ii] to [vi] repeatedly a particular number of times, say in the order of 10 to 100. Here, in an initial traversal, the current treatment plan CTP in step [ii] represents an initial treatment plan for the treatment volume 310, i.e. a default plan is applied. Then, in each traversal subsequent to the initial traversal, the current treatment plan CTP is set equal to the updated treatment plan UTP obtained in a preceding traversal, and so on.

The initial treatment plan used in step [ii] in the first traversal of the procedure preferably represents one of the following: a treatment plan that involves delivering uniform fluence profiles scaled such that an average radiation dose in the at least one target equals a highest prescription level of the respective prescribed radiation doses; a treatment plan that involves delivering no radiation to the treatment volume 310, or a treatment plan that involves delivering radiation to the treatment volume 310 according to a previously generated output radiation treatment plan for the treatment volume 310.

Naturally, these initial treatment plans may require some iterations before converging into a useful updated treatment plan UTP. However, typically, an updated treatment plan UTP that can serve as a basis for the output treatment plan is obtained significantly earlier than when steps [ii] to [vi] have been traversed said particular number of times.

More precisely, it is advantageous if the data processor 110 is configured to generate the output radiation treatment plan P by completing at least one of the optimization phases: a fluence-map optimization phase, a leaf-sequencing optimization phase and a direct-machine-parameter optimization phase, and apply steps [i] to [v] during execution of optimization phase(s) in question.

In the fluence-map optimization phase, fluence per bixel are variables in the optimization process. Each bixel is here a surface element of a discretization of the exposed fluence region 410 on a rectilinear grid in which the rows are aligned with a direction of travel T for the collimator leaves 400-1, 400-2, ..., 400-(n−1), 400-n in the MLC 400. Preferably, the data processor 110 is configured to calculate a set of field delivery times. Each delivery time per field is here a maximum delivery time per row of bixels. The delivery time per row of bixels, in turn, is calculated as a sum of the delivery time for each bixel in the row. The delivery time per bixel is calculated as a sum of a leaf traversal time of the bixel and a positive difference between the irradiation time of the bixel and an irradiation time of a preceding bixel with respect to the direction of travel T for the collimator leaves 400-1, 400-2, ..., 400-(n−1), 400-n. The irradiation time for a bixel is defined as a fluence in the bixel divided by a dose rate of the radiation therapy machine 300, or more precisely the dose rate of the radiation source 305 therein. The leaf traversal time of the bixel is defined as a width of the bixel along the direction of travel T divided by a maximum leaf speed of the radiation therapy machine 300.

In the leaf-sequencing optimization phase, leaf event times are variables in the optimization process. Here, each of said leaf event times defines a respective point in time when each leaf arrives at and leaves a bixel edge. Preferably, the data processor 110 is here configured to determine a field delivery time calculated as a duration from a first leaf event until a last leaf event.

In the direct-machine-parameter optimization phase, leaf positions, dose rate and delivery time per control point are variables in the optimization process. Preferably, the data processor 110 is here configured to calculate field delivery times as a sum of control point delivery times for a set of control points that belong to the field. The set of control points, in turn, are the variables in the optimization process.

In some situations, the upper bound on the modulation efficiency may prove to be unfortunately selected with respect to other constraints in the overall optimizing process. Therefore, according to one embodiment of the invention, the data processor 110 is configured to mitigate the upper bound on the modulation efficiency of the updated treatment plan UTP by introducing a penalty term in the objective function for the optimization. The penalty term measures a deviation from satisfying the upper bound on the modulation efficiency of the updated treatment plan UTP. Consequently, the bound designated by the numerical value ME may be exceeded somewhat given that the output radiation treatment plan P is otherwise appropriate.

According to embodiments of the invention, the data processor 110 is configured to execute the optimization process under a first or a second process. In the first process, the upper bound on the modulation efficiency is implemented with respect to a delivery time calculated as a sum of the delivery times for all fields and an un-modulated delivery time calculated as the sum of the un-modulated delivery times for all fields. In the second process, however, the upper bound on the modulation efficiency is implemented with respect to delivery time calculated as a sum of the delivery times for a subset of the fields and an un-modulated delivery time calculated as the sum of the un-modulated delivery times for the same subset of the fields.

The data processor 110 preferably contains, or is in communicative connection with a memory unit 115 storing a computer program product SW, which contains software for making the data processor 110 execute the above-described actions when the computer program product SW is run on the data processor 110.

As mentioned above, the delivery time is directly proportional to number of MUs delivered over a treatment fraction provided that the machine dose rate is constant. If, however, the radiation therapy machine 300 supports a variable dose rate, then the complexity bounds can be defined relative to the number of MUs instead of the delivery time. According to the invention, such an MU-type of complexity bound can be implemented simultaneously with the proposed complexity bound on treatment time.

Figure 5:
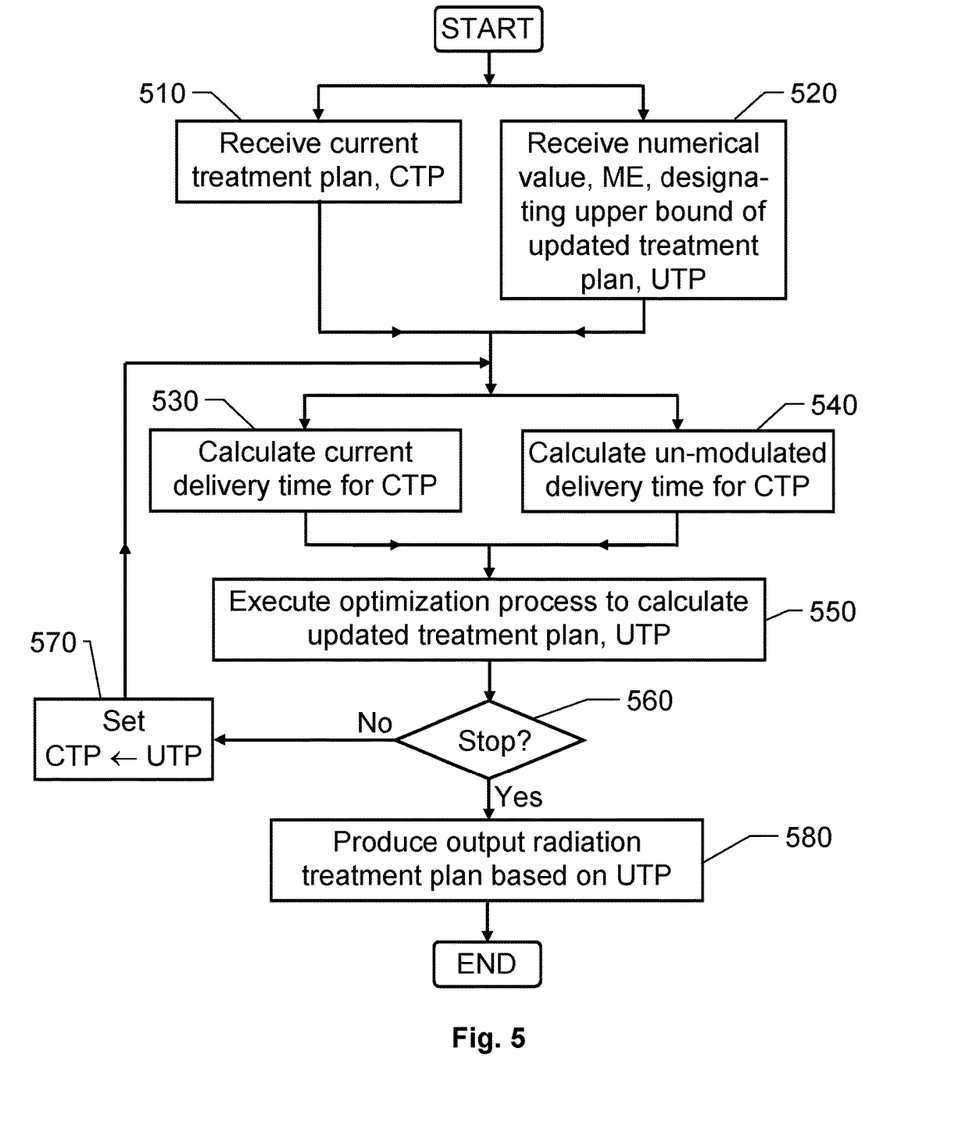
FIG. 5 illustrates, by means of a flow diagram, the general method according to the invention for determining an output radiation treatment plan.

In order to sum up, and with reference to the flow diagram in FIG. 5, we will now describe the general method executed in the data processor 110 according to the invention when generating an output radiation treatment plan P for a treatment volume 310 associated with at least one target, where each of the at least one target is associated with a respective prescribed radiation dose.

A step 510 receives a current treatment plan CTP. In parallel with, before or after step 510, a step 520 receives a numerical value ME designating an upper bound on modulation efficiency of an updated treatment plan UTP. The updated treatment plan UTP will, when implemented by a radiation therapy machine 300, cause the respective prescribed radiation dose to be delivered to the at least one target. The updated treatment plan UTP is presumed to require an updated delivery time $T_{UTP}$ to complete.

After steps 510 and 520, a step 530 calculates a current delivery time $T_{CTP}$ for the current treatment plan CTP. After steps 510 and 520; in parallel with, before or after step 530; a step 540 calculates an un-modulated delivery time $T_{UM}$ for the current treatment plan CTP.

Subsequently, i.e. after steps 530 and 540, a step 550 calculates the updated treatment plan UTP by executing an optimization process while satisfying the upper bound on the modulation efficiency given by ME.

A step 560 thereafter checks if a stop criterion if fulfilled, e.g. that steps 530 to 550 have been traversed a predetermined number of times. If the stop criterion is fulfilled, a step 580 follows; and otherwise, the procedure continues to a step 570, wherein the current treatment plan CTP is set equal to the updated treatment plan UTP that was calculated in step 550. Then, the procedure loops back to steps 530 and 540.

In step 580, an output radiation treatment plan P is generated based on the updated treatment plan UTP. After step 580, the procedure ends.

All of the process steps, as well as any sub-sequence of steps, described with reference to FIG. 5 above may be controlled by means of a programmed computer apparatus. Moreover, although the embodiments of the invention described above with reference to the drawings comprise a computer apparatus and processes performed in a computer apparatus, the invention thus also extends to computer programs, particularly computer programs on or in a carrier, adapted for putting the invention into practice. The program may be in the form of source code, object code, a code intermediate to source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A system for generating an output radiation treatment plan for a treatment volume associated with at least one target, each of the at least one target being associated with a respective prescribed radiation dose, the system comprising:
a data processor configured to:
calculate an updated treatment plan which when implemented by a radiation therapy machine is configured to cause the respective prescribed radiation dose to be delivered to the at least one target, the updated treatment plan requiring an updated delivery time to complete,
wherein the data processor is configured to:
[i] receive a numerical value designating an upper bound on modulation efficiency of the updated treatment plan,
[ii] receive a current treatment plan,
[iii] calculate a current delivery time for the current treatment plan,
[iv] calculate an un-modulated delivery time for the current treatment plan,
[v] calculate the updated treatment plan by executing an optimization process while satisfying the upper bound on the modulation efficiency, and
[vi] generate the output radiation treatment plan based on the updated treatment plan.

2. The system according to claim 1, wherein the un-modulated delivery time is calculated based on an un-modulated delivery time per field of the current treatment plan, each of which is a time required to deliver an un-modulated field with an exposed fluence region equal to an exposed fluence region for the field of the current treatment plan, a fluence inside the exposed fluence region of the un-modulated field having a constant value being scaled such that an average fluence is equal to an average fluence inside the exposed fluence region for the field of the current treatment plan, the exposed fluence region being a sub-region of a beam plane to be exposed by an opening between a set of collimator leaves in a multi-leaf collimator of the radiation therapy machine during delivery of the field.

3. The system according to claim 2, wherein the upper bound on the modulation efficiency represents a quotient between the updated delivery time and the un-modulated delivery time, and the upper bound on the modulation efficiency is satisfied if the modulation efficiency is less than or equal to the numerical value.

4. The system according to claim 2, wherein the data processor is configured to traverse steps [ii] to [vi] repeatedly a particular number of times where:
in an initial traversal, the current treatment plan represents an initial treatment plan for the treatment volume, and
in each traversal subsequent to the initial traversal, the current treatment plan is the updated treatment plan obtained in a preceding traversal.

5. The system according to claim 4, wherein the initial treatment plan represents one of:
delivering uniform fluence profiles scaled such that an average radiation dose in the at least one target equals a highest prescription level of the respective prescribed radiation doses,
delivering no radiation to the treatment volume, or
delivering radiation to the treatment volume according to a previously generated output radiation treatment plan for the treatment volume.

6. The system according to claim 2, wherein the data processor is configured to generate the output radiation treatment plan by completing at least one of the optimization phases:
a fluence-map optimization phase, wherein fluence per bixel are variables in the optimization process, each bixel being a surface element of a discretization of the exposed fluence region on a rectilinear grid in which the rows are aligned with a direction of travel for the collimator leaves in the multi-leaf collimator;
a leaf-sequencing optimization phase, wherein leaf event times are variables in the optimization process, each of said leaf event times defining a respective point in time when each leaf arrives at and leaves a bixel edge; and
a direct-machine-parameter optimization phase, wherein leaf positions, dose rate and delivery time per control point are variables in the optimization process; and
the data processor is configured to apply steps [i] to [v] during execution of at least one of said at least one optimization phases.

7. The system according to claim 6, wherein:
in the fluence-map optimization phase, the data processor is configured to calculate a set of field delivery times, each delivery time per field being a maximum delivery time per row of bixels, the delivery time per row of bixels being calculated as a sum of the delivery time for each bixel in the row, the delivery time per bixel being calculated as a sum of a leaf traversal time of the bixel and a positive difference between the irradiation time of the bixel and an irradiation time of a preceding bixel with respect to the direction of travel for the collimator leaves, the irradiation time for a bixel being defined as a fluence in the bixel divided by a dose rate of the radiation therapy machine, and the leaf traversal time of the bixel being defined as a width of the bixel along the direction of travel divided by a maximum leaf speed of the radiation therapy machine;

in the leaf-sequencing optimization phase, the data processor is configured to determine a field delivery time calculated as a duration from a first leaf event until a last leaf event; and in the direct-machine-parameter optimization phase, the data processor is configured to calculate field delivery times as a sum of control point delivery times for a set of control points that belong to the field, the set of control points being the variables in the optimization process.

8. The system according to claim 7, wherein the data processor is configured to mitigate the upper bound on the modulation efficiency of the updated treatment plan by introducing a penalty term in the objective function that is to be minimized by the optimization, the penalty term measuring a deviation from satisfying the upper bound on the modulation efficiency of the updated treatment plan.

9. The system according to claim 1, wherein the data processor is configured to execute the optimization process under at least one of:

a first process wherein the upper bound on the modulation efficiency is implemented with respect to a delivery time calculated as a sum of the delivery times for all fields and an un-modulated delivery time calculated as the sum of the un-modulated delivery times for all fields; and a second process wherein the upper bound on the modulation efficiency is implemented with respect to delivery time calculated as a sum of the delivery times for a subset of the fields and an un-modulated delivery time calculated as the sum of the un-modulated delivery times for the same subset of the fields.

10. The system according to claim 1, wherein the upper bound on the modulation efficiency comprises a constraint on a set of optimization variables in addition to a number of constraints associated with causing the prescribed radiation dose to be delivered to the at least one target while aiming at not delivering more than a threshold amount of radiation to at least one organ-at-risk.

11. A method of generating an output radiation treatment plan for a treatment volume associated with at least one target, each of the at least one target being associated with a respective prescribed radiation dose, the method comprising:

calculating an updated treatment plan which when implemented by a radiation therapy machine is configured to cause the respective prescribed radiation dose to be delivered to the at least one target, the updated treatment plan requiring an updated delivery time to complete,

[i] receiving a numerical value designating an upper bound on modulation efficiency of the updated treatment plan,

[ii] receiving a current treatment plan,

[iii] calculating a current delivery time for the current treatment plan,

[iv] calculating an un-modulated delivery time for the current treatment plan,

[v] calculating the updated treatment plan by executing an optimization process while satisfying the upper bound on the modulation efficiency, and

[vi] generating the output radiation treatment plan based on the updated treatment plan.

12. The method according to claim 11, wherein the un-modulated delivery time is calculated based on an un-modulated delivery time per field of the current treatment plan, each of which is a time required to deliver an un-modulated field with an exposed fluence region equal to an exposed fluence region for the field of the current treatment plan, a fluence inside the exposed fluence region of the un-modulated field having a constant value being scaled such that an average fluence is equal to an average fluence inside the exposed fluence region for the field of the current treatment plan, the exposed fluence region being a sub-region of a beam plane to be exposed by an opening between a set of collimator leaves in a multi-leaf collimator of the radiation therapy machine during delivery of the field.

13. The method according to claim 12, wherein the upper bound on the modulation efficiency represents a quotient between the updated delivery time and the un-modulated delivery time, and the upper bound on the modulation efficiency is satisfied if the modulation efficiency is less than or equal to the numerical value.

14. The method according to claim 12, wherein steps [ii] to [vi] are traversed repeatedly a particular number of times, where:

in an initial traversal, the current treatment plan represents an initial treatment plan for the treatment volume, and in each traversal subsequent to the initial traversal, the current treatment plan is the updated treatment plan obtained in a preceding traversal.

15. The method according to claim 14, wherein the initial treatment plan represents one of:

delivering uniform fluence profiles scaled such that an average radiation dose in the at least one target equals a highest prescription level of the respective prescribed radiation doses, delivering no radiation to the treatment volume, or delivering radiation to the treatment volume according to a previously generated output radiation treatment plan for the treatment volume.

16. The method according to claim 12, comprising generating the output radiation treatment plan by completing at least one of the optimization phases:

a fluence-map optimization phase, wherein fluence per bixel are variables in the optimization process, each bixel being a surface element of a discretization of the exposed fluence region on a rectilinear grid in which the rows are aligned with the direction of travel for the collimator leaves in the multi-leaf collimator;

a leaf-sequencing optimization phase, wherein leaf event times are variables in the optimization process, each of said leaf event times defining a respective point in time when each leaf arrives at and leaves a bixel edge; and a direct-machine-parameter optimization phase, wherein leaf positions, dose rate and delivery time per control point are variables in the optimization process; and the data processor is configured to apply steps [i] to [v] during execution of at least one of said at least one optimization phases.

17. The method according to claim 16, wherein:
- in the fluence-map optimization phase, the method comprises calculating a set of field delivery times, each delivery time per field being a maximum delivery time per row of bixels, the delivery time per row of bixels being calculated as a sum of the delivery time for each bixel in the row, the delivery time per bixel being calculated as a sum of a leaf traversal time of the bixel and a positive difference between the irradiation time of the bixel and an irradiation time of a preceding bixel with respect to the direction of travel for the collimator leaves, the irradiation time for a bixel being defined as a fluence in the bixel divided by a dose rate of the radiation therapy machine, and the leaf traversal time of the bixel being defined as a width of the bixel along the direction of travel divided by a maximum leaf speed of the radiation therapy machine;
- in the leaf-sequencing optimization phase, the method comprises determining a field delivery time calculated as a duration from a first leaf event until a last leaf event; and
- in the direct-machine-parameter optimization phase, the method comprises calculating field delivery times as a sum of control point delivery times for a set of control points that belong to the field, the set of control points being the variables in the optimization process.

18. The method according to claim 17, comprising mitigating the upper bound on the modulation efficiency of the updated treatment plan by introducing a penalty term in the objective function that is to be minimized by the optimization, the penalty term measuring a deviation from satisfying the upper bound on the modulation efficiency of the updated treatment plan.

19. The method according to claim 11, comprising executing the optimization process under at least one of:
- a first process wherein the upper bound on the modulation efficiency is implemented with respect to a delivery time calculated as a sum of the delivery times for all fields and an un-modulated delivery time calculated as the sum of the un-modulated delivery times for all fields; and
- a second process wherein the upper bound on the modulation efficiency is implemented with respect to delivery time calculated as a sum of the delivery times for a subset of the fields and an un-modulated delivery time calculated as the sum of the un-modulated delivery times for the same subset of the fields.

20. The method according to claim 11, wherein the upper bound on the modulation efficiency comprises a constraint on a set of optimization variables in addition to a number of constraints associated with causing the prescribed radiation dose to be delivered to the at least one target while aiming at not delivering more than a threshold amount of radiation to at least one organ-at-risk.

21. A radiation therapy machine configured to:
- receive an output radiation treatment plan determined by the method according to claim 11, and
- carry out therapy in respect of a treatment volume by controlling a radiation source in accordance with the output radiation treatment plan.

22. A computer program product loadable into a memory of at least one computer, comprising software for performing the steps of the method according to claim 11 when executed on the at least one computer.

23. A computer readable medium having a program recorded thereon, where the program is to make at least one computer perform the steps of claim 11.

24. A radiation therapy method comprising: receiving an output radiation treatment plan determined by the method according to claim 11, and carrying out therapy in respect of a treatment volume by controlling a radiation source in accordance with the output radiation treatment plan.

* * * * *